United States Patent [19]

Majoie

[11] 4,229,439
[45] Oct. 21, 1980

[54] METHOD OF TREATMENT OF ATHEROMA

[75] Inventor: Bernard Majoie, Dijon, France

[73] Assignee: Societe de Recherches Industrielles (SORI), Paris, France

[21] Appl. No.: 853,422

[22] Filed: Nov. 21, 1977

[51] Int. Cl.³ .................. A61K 31/70; C07H 17/06
[52] U.S. Cl. .................................. 424/180; 536/8
[58] Field of Search ........................ 424/180; 536/8

[56] References Cited

U.S. PATENT DOCUMENTS

| 2,744,893 | 5/1956 | Wender et al. | 536/8 |
|---|---|---|---|
| 3,422,086 | 1/1969 | Carron et al. | 536/8 |
| 3,888,842 | 6/1975 | Cazaux et al. | 536/8 |

Primary Examiner—Johnnie R. Brown
Attorney, Agent, or Firm—Bacon & Thomas

[57] ABSTRACT

This invention is concerned with a new method of treatment for reducing retention of cholesterol, e.g., in the treatment of atheroma and angiopathies which comprises administering to a patient in need of such treatment, a therapeutically effective amount of at least one anthocyanidin compound of the general formula

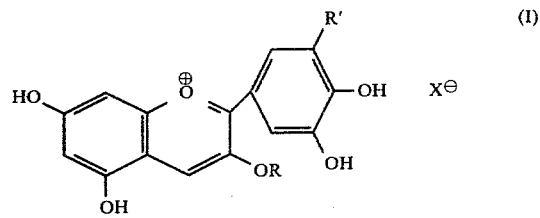

wherein R represents a glycosyl group such as glycosyl or rhamnoglucosyl; R' represents H, OH or OCH₃; and X⁻ is a non-toxic anion such as chloride, citrate, tartrate, phosphate or malate.

6 Claims, No Drawings

METHOD OF TREATMENT OF ATHEROMA

BACKGROUND OF THE INVENTION

The anthocyanidins of formula I are known per se and have been obtained by extraction and purification from flowers (for instance from winter aster, violet, petunia, pansy, euphorbia) and from fruit or the skin thereof (for instance from sweet and sour cherries, strawberries, cranberries, whortleberries, blackcurrants). They have also been proposed for use in the therapeutical field as agents (i) having a vitamin-like action (see U.S. Pat. No. 2,744,893) or prolonging the retention of vitamin C (see U.S. Pat. No. 2,647,058) and (ii) improving the resistance and the permeability of capillaries (see French BSM No. 6760M) and therefore being useful for improving visual acuity by night (see British Pat. No. 1,007,751).

It has now been found that anthocyanidin compounds of formula I (i) reduce the retention of cholesterol in arteries, (ii) improve the collagen synthesis which is disturbed by hypertension and diabetes, and (iii) normalize the flexibility and deformability of red blood cells in patients suffering from artery disorders, and that said anthocyanidin compounds are surprisingly useful and efficient in the treatment of heart and artery disorders such as atheroma and, in a general manner, angiopathies (i.e. impairment of the vascular wall especially in connection with hypertension diabetes, and other metabolic diseases and/or ischaemiae resulting therefrom).

SUBJECT OF THE INVENTION

The subject of the invention is to propose a net method of treatment for reducing retention of cholesterol in arteries which is useful in e.g. the treatment of atheroma and angiopathies by administering for that purpose an anthocyanidin compound or a mixture of anthocyanidin compounds.

Said method of treatment comprises administering to a patient in need of such treatment, a therapeutically effective amount of at least one anthocyanidin compound of the general formula

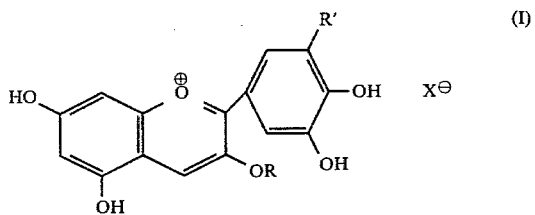

wherein R represents H or a glycosyl group; R' represents H, OH, OCH$_3$; and X$^-$ is a non-toxic anion.

The preferred glycosyl groups according to this invention are glycosyl and rhamnoglucosyl. The anion X$^-$ generally depends on the mode of extraction and isolation of the anthocyanidin compounds, for example X$^-$ may represent Cl$^-$, $\frac{1}{3}$PO$_4^{3-}$, $\frac{1}{2}$HPO$_4^{2-}$, H$_2$PO$_4^-$, or a malate, tartrate, or citrate anion.

The preferred anion is the chloride.

The best mode for carrying out the method of treatment of this invention consists in administering by oral route or by injection a daily dose from 25 mg to 300 mg of at least one anthocyanidin compound of formula I.

The duration of the treatment is preferably comprised between 2 and 4 weeks.

DETAILED DESCRIPTION OF THE INVENTION

According to the above definitions, formula I includes within its scope the following compounds:

(i) the cyanidin compounds wherein R' is H, namely
 the cyanidin salts (R=H) and in particular cyanidin chloride (II) which is 2-(3,4-dihydroxyphenyl)-3,5,7-trihydroxy-1-benzopyrylium chloride,
 the cyanidin-3-glucoside salts (R=glycosyl) and in particular cyanidin-3-glucoside chloride (III),
 the cyanidin-3-rhamnoglucoside salts (R=rhamnoglucosyl) and in particular cyanidin-3-rhamnoglucoside chloride (IV);

(ii) the delphinidin compounds when R' is OH, namely
 the delphinidin salts (R=H) and in particular delphinidin chloride (V) which is 2-(3,4,5-trihydroxyphenyl)-3,5,7-trihydroxy-1-benzopyrylium chloride,
 the delphinidin-3-glucoside salts (R=glucosyl) in particular delphinidin-3-glucoside chloride (VI)
 the delphinidin-3-rhamnoglucoside salts (R=rhamnoglucosyl) in particular delphinidin-3-rhamnoglucoside chloride (VII); and (iii) the petunidin compounds when R' is OCH$_3$, namely
 the petunidin salts (R=H in particular petunidin chloride (VIII) which is 2-(3,4-dihydroxy-5-methoxyphenyl)-3,5,7-trihydroxy-1-benzopyrylium chloride,
 the petunidin-3-glucoside salts (R=glucosyl) in particular petunidin-3-glucoside chloride (IX) and
 the petunidin-3-rhamnoglucoside salts (R=rhamnoglucosyl) in particular petunidin-3-rhamnoglucoside chloride (X).

Anthocyanidins III, IV, VI, VII and IX are natural products which are present for instance in grapes. They can be extracted singly or together and if necessary isolated, according to a method known per se, from flowers and fruit containing them. In particular, the mixture of III, IV, VI and VII can be obtained in large quantity from blackcurrant, and IX can be obtained pure from certain flowers wherein it is almost the only anthocyanidin compound.

Where an anthocyanidin is found pure and as the only anthocyanidin in the plant (which is the case of petunidin derivatives in flowers, and also of delphinidin derivatives in aubergines for example), the extraction followed by a mere purification leads to the desired products with a degree of purity of 99% or more.

Where mixtures of anthocyanidins are present in one and the same natural species (which is the case with compounds III, IV, VI and VII in blackcurrants), first the anthocyanic mixture is extracted (from blackcurrant concentrated juices or marcs for example) according to a method known per se. Then, in an anion exchanging column or in a polyvinylpyrrolidone column, and in accordance with the methods described in the literature, a separation is made of each of the constituents of the anthocyanic mixture, i.e. in the specific case of blackcurrants, the mixture III+IV+VI+VIII.

As to compounds II, V, and VII these are three genins obtained very easily by acid hydrolysis (HCl) of either one, or even of the mixture, of the corresponding oside-containing derivatives. For example, II is obtained by acid hydrolysis of III, of IV or of the mixture III+IV.

The compounds of formula I have a remarkable action useful in the treatment of atheroma and angiopathies in particular:

by inhibiting the retention of cholesterol circulating in arteries: the mechanism being probably that of an inhibition of the complexing between atherogenic lipoproteins and tissular and cellular polysaccharide macromolecules;

by normalizing, after treatment, the perturbation in the synthesis of collagen, which disturbance is initiated by hypertension, by the fatty plaque, by diabetes; in this way, the collagen synthesis in the aorta of the hypercholesterolemic, hypertensive or diabetic (induced by Streptozotocin)rat is normalized under the effect of the compounds of formula I; said normalization was estimated from the quantity of collagen and of the various solubilized fractions;

by a considerable improvement of the oxygenation in disorders such as atherosclerosis, by normalizing the flexibility of the red blood cells and their deformability; it was indeed demonstrated (see hereinafter) that the said deformability is reduced in pathological conditions initiatory to atherosclerosis: hypercholesterolemia, hypertension, diabetes.

The pharmacological tests and their results are summarized hereinafter. For convenience, the tests were carried out using the chlorides II—IX and one of their mixtures, namely the mixture III+IV+VI+VII. This mixture was obtained in the pure state from blackcurrants according to the method described by T. FULEKI et al. in J. Fed. Sci., (1968), 33, 266. In this purified mixture the average amounts of the four compounds are:

III: about 9% by weight
IV: about 44% by weight
VI: about 12% by weight
VII: about 35% by weight The percentages are average values since the respective proportions of each product vary slightly as a function of the year of the crop.

(a) Toxicity

The LD-50 values have been determined on rats by I.P. route according to the method of J. T. LITCHFIELD et al., J. Pharmacol. Exptl. Therap. (1949), 96, 99. The data in table I show that the anthocyanidin compounds according to this invention are not toxic since their LD-50 is comprised between 1,000 mg/kg and 2,000 mg/kg.

TABLE I

| Compound | LD-50 i.P. rats mg/kg |
| --- | --- |
| II | 1,500 |
| III | 2,000 |
| IV | 1,900 |
| V | 1,250 |
| VI | 1,850 |
| VII | 1,900 |
| VIII | 1,000 |
| IX | 1,750 |
| mixture III + IV + VI + VII | 1,900 |

(b) Inhibition of cholesterol retention

The tests were carried out in vivo on two pathological types of perturbation of the lipidic parameters initiated in:

rats made hyperlipemic by administration of a fatty diet composed as follows: 20 parts by weight of casein, 6 parts by weight of alphacel, 40 parts by weight of lard, 2 parts by weight of cholesterol, 0.25 parts by weight of choline chloride, one part by weight of cholic acid, 12 parts by weight of sucrose, 12 parts by weight of starch and vitamins (traces);

rats made hypertensive according to the Goldblatt et al. method, J. Exp. Med. (1934), 59, 347-379.

In each case, the tests were carried out on two groups of 10 rats (one test group and one control group). The animals treated were given the product at the rate of 50 mg/kg IP, three times a week for 3 weeks.

At the end of the test, the animals were sacrificed, the aortas recovered and the total cholesterol measured, according to the method of C. C. HEUCK et al., J. Lip. Res., (1977), 18, 259, after extraction by gas chromatography.

The results are given in Table II in % reduction of the total cholesterol noted in the treated animals compared with the controls receiving the hyperlipidic diet or made hypertensive.

TABLE II

| COMPOUND | Rats fed a fatty diet % Reduction of cholesterol | Hypertensive Rats % Reduction of cholesterol |
| --- | --- | --- |
| II | 18 | 16 |
| III | 26 | 29 |
| IV | 25 | 31 |
| V | 15 | 17 |
| VI | 29 | 33 |
| VII | 31 | 30 |
| VIII | 17 | 16 |
| IX | 27 | 28 |
| Mixture III + IV + VI + VII | 28 | 31 |

(c) Deformability of the red blood cells

The activity was determined in vivo in a monkey made hyperlipidemic after absorption of a fatty diet. The compounds to be tested were given per os at the rate of 100 mg daily for 6 months, to groups of 10 monkeys each: one group receiving a normal diet, one group receiving a fatty diet, the other groups receiving the fatty diet and one of the compounds to be tested. The results given in Table III are average values of the speed of filtration of the erythrocytes in ml/10 secs. The statistical means of the results are very good ($p > 0.05$).

TABLE III

| | ERYTHROCYTES FILTERING SPEED | | |
| --- | --- | --- | --- |
| COMPOUND | NORMAL DIET | FATTY DIET | FATTY DIET + TREATMENT |
| II | 2.098 | 1.701 | 1.805 |
| III | 2.266 | 1.795 | 2.261 |
| IV | 2.098 | 1.638 | 2.088 |
| V | 2.166 | 1.756 | 1.902 |
| VI | 2.144 | 1.721 | 2.097 |
| VII | 2.221 | 1.788 | 2.189 |
| VIII | 2.254 | 1.804 | 1.921 |
| IX | 2.157 | 1.704 | 2.101 |
| III + IV + VI + VII | 2.046 | 1.647 | 1.998 |

As a result of the foregoing, the anthocyanidins according to the invention favorably protect the arterial wall with respect to lipidic infiltration. The anthocyanidins according to the invention may be administered in a pharmacologically acceptable excipient, according to non-restrictive examples given hereunder:

Example 1

The active compound is mixed with cellulose, starch and magnesium stearate. The mixture obtained is compressed so as to obtain cuttable tablets containing 50 mg of active substance.

Example 2

The active compound is mixed with lactose and icing sugar. The mixture obtained is granulated by a fluidized bed process and then mixed with magnesium stearate and compressed so as to obtain sublingual tablets, containing 50 mg of active substance.

Example 3

An injectable composition is prepared, for immediate use, from 50 mg of the lyophilized and sterile active compound and 3 ml of water for injectable solution.

Finally, compound III was tested for 21 days in 50 patients (25 being hyperlipidic patients and the other 25 suffering from arterial hypertension), one group of patients receiving 3 tablets or 3 sublingual tablets daily, dosed at 50 mg each, the other group receiving one injection daily of 50 mg of compound III. The tolerance proved to be excellent since the condition of 40 patients (i.e. 80%) was noticeably improved.

What is claimed is:

1. A method for reducing retension of cholesterol in arteries which comprises administering to a patient in need of such a treatment, a therapeutically effective amount of at least one anthocyanidin compound which is a salt of the cation of the formula

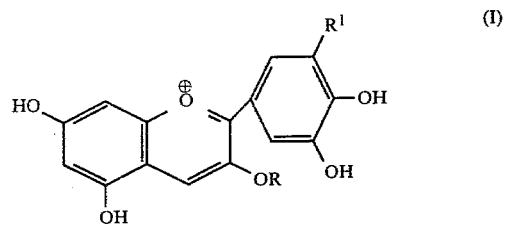

wherein R represents a glycosyl group and $R^1$ represents H, OH or $OCH_3$; and a non-toxic anion.

2. The method according to claim 1 wherein R is glucosyl or rhamnoglucosyl.

3. The method according to claim 1 wherein the anion is chloride.

4. The method according to claim 1 wherein the anion is citrate, tartrate, phosphate or malate.

5. The method according to claim 1 wherein a daily dose from 25 mg to 300 mg of at least one chloride of the cation of formula I in which R is glucosyl or rhamnoglucosyl is administered.

6. The method according to claim 1 which is a method for treating atheroma.

* * * * *